US011540734B2

(12) United States Patent
DeBusschere et al.

(10) Patent No.: US 11,540,734 B2
(45) Date of Patent: Jan. 3, 2023

(54) APPARATUS FOR NONINVASIVE MEASUREMENT OF A HEART PERFORMANCE METRIC

(71) Applicant: Verily Life Sciences LLC, South San Francisco, CA (US)

(72) Inventors: Derek DeBusschere, Los Gatos, CA (US); Benjamin K. Yaffe, San Francisco, CA (US); Shannon Fong, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 481 days.

(21) Appl. No.: 16/551,362

(22) Filed: Aug. 26, 2019

(65) Prior Publication Data

US 2020/0060561 A1    Feb. 27, 2020

Related U.S. Application Data

(60) Provisional application No. 62/723,242, filed on Aug. 27, 2018.

(51) Int. Cl.
*A61B 5/022* (2006.01)
*A61B 5/024* (2006.01)
(Continued)

(52) U.S. Cl.
CPC ...... *A61B 5/02241* (2013.01); *A61B 5/02416* (2013.01); *A61B 5/0205* (2013.01); *A61B 5/02116* (2013.01); *A61B 5/02225* (2013.01)

(58) Field of Classification Search
None
See application file for complete search history.

(56) References Cited

U.S. PATENT DOCUMENTS 3,776,221 A    12/1973    McIntyre
3,908,639 A     9/1975    McIntyre
(Continued)

FOREIGN PATENT DOCUMENTS

KR    101042827 B1    6/2011
WO    2017143366 A1   8/2017

OTHER PUBLICATIONS

Bernardi, L., et al., "Do Hemodynamic Responses to the Valsalva Maneuver Reflect Myocardial Dysfunction?" Chest 95:986-991, 1989.
(Continued)

*Primary Examiner* — Allen Porter
*Assistant Examiner* — Samuel C Kim
(74) *Attorney, Agent, or Firm* — Christensen O'Connor Johnson Kindness PLLC

(57) ABSTRACT

An apparatus for measuring a performance metric of a heart includes a housing, a tactile sensor, a finger clamp, a linear actuator, and a controller. The tactile sensor measures blood pressure pulsatility in a digital artery of a finger via applanation tonometry and outputs pulsatility signals indicative of the blood pressure pulsatility. The finger clamp extends from the housing to clamp the finger against the tactile sensor with the digital artery aligned over the tactile sensor. The linear actuator drives the finger clamp with a clamping force directed along a linear path. The controller is coupled to the tactile sensor and the linear actuator to control the clamping force and to generate pulsatility data, based upon the pulsatility signals, from which the performance metric of the heart may be determined.

22 Claims, 12 Drawing Sheets

(51) Int. Cl.
*A61B 5/0205* (2006.01)
*A61B 5/021* (2006.01)

(56) References Cited

U.S. PATENT DOCUMENTS

| | | | |
|---|---|---|---|
| 5,291,895 A | 3/1994 | McIntyre | |
| 6,610,018 B1 | 8/2003 | McIntyre | |
| 7,404,800 B2 | 7/2008 | McIntyre | |
| 9,044,146 B2* | 6/2015 | Jeon | A61B 5/021 |
| 9,549,678 B2 | 1/2017 | Silber | |
| 2006/0005631 A1* | 1/2006 | Hashimoto | A61B 5/02116 73/780 |
| 2006/0009700 A1* | 1/2006 | Brumfield | A61B 5/6838 600/587 |
| 2010/0168531 A1 | 7/2010 | Shaltis et al. | |
| 2011/0245691 A1* | 10/2011 | Silber | A61B 5/6838 600/485 |
| 2016/0206231 A1* | 7/2016 | Kun | A61B 5/14552 |
| 2018/0206746 A1 | 7/2018 | Narasimhan et al. | |
| 2019/0053723 A1* | 2/2019 | van Sparrentak | A61B 5/02208 |
| 2019/0150765 A1* | 5/2019 | Fortin | A61B 5/02255 |

OTHER PUBLICATIONS

Bernardi, L., et al., "Noninvasive Assessment of Central Circulatory Pressures by Analysis of Ear Densitographic Changes During the Valsalva Maneuver," American Journal of Cardiology 64:787-792, 1989.

Forfia, P.R., "Blood Pressure Response to the Valsalva Maneuver: A Simple Bedside Test to Determine the Hemodynamic Basis of Pulmonary Hypertension," Journal of the American College of Cardiology—Correspondence 56(16):1352-1353, 2010.

Galiatsatos, P., et al., A Finger Photoplethysmography Waveform During the Valsalva Maneuver Detects Changes in Left Heart Filling Pressure After Hemodialysis, BMC Nephrology 16:138, 2015, 7 pages.

Galiatsatos, P., "A Noninvasive, Hand-Held Device for Assessing Left Ventricular End-Diastolic Pressure Based on Finger Photoplethysmography and the Valsalva Maneuver," PowerPoint Presentation, Feb. 2, 2013, Johns Hopkins Bayview Medical Center, 21 pages.

Galiatsatos, P., et al., "A Noninvasive, Hand-Held Device for Assessing Left Ventricular End-Diastolic Pressure Based on Finger Photoplethysmography and the Valsalva Maneuver," Journal of the American College of Cardiology vol. 67, Issue 13 Supplement, Apr. 2016, 1-page abstract.

Galiatsatos, P., et al., "Usefulness of a Noninvasive Device to Identify Elevated Left Ventricular Filling Pressure Using Finger Photoplethysmography During a Valsalva Maneuver," American Journal of Cardiology 119(7):1053-1060, Apr. 2017.

Gillard, C., et al., "Operating Characteristics of the Finapress System to Predict Elevated Left Ventricular Filling Pressure," Clinical Cardiology 29:107-111, 2006.

Givertz, M.M., et al., "Noninvasive Determination of Pulmonary Artery Wedge Pressure in Patients With Chronic Heart Failure," American Journal of Cardiology 87:1213-1215, May 2001.

Hébert, J.-L., et al., "Pulse Pressure Response to the Strain of the Valsalva Maneuver in Humans With Preserved Systolic Function," Journal of Applied Physiology 85(3):817-823, 1998.

Marik, P.E., "The Systolic Blood Pressure Variation as an Indicator of Pulmonary Capillary Wedge Pressure in Ventilated Patients," Anaesthesia and Intensive Care 21(4):405-408, Aug. 1993; 1-page abstract.

McIntyre, K.M., et al., "Validation and Clinical Applications of a Non-Invasive Valsalva Response Recorder," Journal of Applied Cardiology 2(2):137-169, 1987.

McIntyre, K.M., et al., "A Noninvasive Method of Predicting Pulmonary-Capillary Wedge Pressure," New England Journal of Medicine 327(24):1715-1720, Dec. 1992.

McIntyre, K.M., et al., "Noninvasive Method of Predicting Pulmonary-Capillary Wedge Pressure," letter to the editor, New England Journal of Medicine 327(19):1423-1424, May 1993.

Remmen, J.J., et al., "Normal Values of Pulmonary Capillary Wedge Pressure and the Blood Pressure Response to the Valsalva Manoeuvre in Healthy Elderly Subjects," Clinical Physiology and Functional Imaging 25(6):318-326, Nov. 2005; 3-page abstract.

Remmen, J.J., et al., "Detection of Elevated Polmonary Capillary Wedge Pressure in Elderly Patients With Various Cardiac Disorders by the Valsalva Manoeuvre," Clinical Science 111:153-162, 2006.

Remmen, J., "Non-Invasive Assessment of Pulmonary Capillary Wedge Pressure in the Elderly by the Valsalva Manoeuvre," Master's Thesis, Radboud University Nijmegen, 169 pages.

Sharma, R.G., et al., "Accuracy and Reproducibility of Noninvasively Determined Left Ventricular End Diastolic Pressure in the Catheterization Laboratory and the Office Setting," Abstract 1014-153, JACC, Poster Session, p. 129A, Mar. 6, 2002, 1-page abstract.

Sharma, G.V.R.K., et al., "Evaluation of a Noninvasive System for Determining Left Ventricular Filling Pressure," Archives of Internal Medicine 162(18):2084-2088, Oct. 2002.

Sharma, G.V.R.K., et al., "Noninvasive Tracking of Acute Changes in Left Ventricular End-Diastolic Pressure by the Vericor System," Journal of Cardiac Failure, vol. 8, No. 4 Suppl., abstract 327, p. S88, 2002.

Sharma, G.V.R.K., et al., "Suitability of the VeriCor® System, a Non-Invasive Device That Estimates Left Ventricular End-Diastolic Pressure for Screening Patients at High Risk of Developing Heart Failure," HFSA 7th Annual Scientific Meeting, abstract 424, p. S113, 2003.

Sharma, G.V.R.K., et al., "Left Ventricular End-Diastolic Pressure Guided Treatment of Patients Hospitalized for Heart Failure Reduces Rehospitalization Rate," Journal of Cardiac Failure, vol. 15, No. 6S Suppl., abstract 289, p. S88, 2009.

Sharma, G.V.R.K., et al., "Noninvasive Monitoring of Left Ventricular End-Diastolic Pressure Reduces Rehospitalization Rates in Patients Hospitalized for Heart Failure: A Randomized Controlled Trial," Journal of Cardiac Failure 17(9):718-725, 2011.

Silber, H.A., et al., "Finger Photoplethysmography During the Valsalva Maneuver Reflects Left Ventricular Filling Pressure," American Journal of Physiology Heart and Circulatory Physiology 302(10):H2043-H2047, May 2012.

"Vixiar Indicor™: Point of Care, Non-Invasive, Cost Effective, Solution for Assessing Cardiac Filling Pressure," © 2016 Vixiar, <https://vixiar.com/technology/> [retrieved Jul. 2, 2018], 3 pages.

Uehara, H., et al., "A New Method of Predicting Pulmonary Capillary Wedge Pressure: The Arterial Pressure Ratio," Anaesthesia 55:113-117, 2000.

Van Kraaij, D.J.W., et al., "Use of the Valsalva Manoeuvre to Identify Haemodialysis Patients at Risk of Congestive Heart Failure," Nephrology Dialysis Transplantation 13:1518-1523, 1998.

Weilenmann, D., et al., "Noninvasive Evaluation of Pulmonary Capillary Wedge Pressure by BP Response to the Valsalva Maneuver," Chest 122:140-145, 2002.

Xu, H., et al., "Prediction of Pulmonary Arterian Wedge Pressure From Arterial Pressure or Pulse Oximetry Plethysmographic Waveform," Chinese Medical Journal 115(9):1372-1375, 2002.

Zema, M.J., et al., "Left Ventricular Dysfunction—Bedside Valsalva Manoeuvre," British Heart Journal 44:560-569, 1980.

International Search Report & Written Opinion for corresponding International Application No. PCT/US19/48352, dated Nov. 21, 2019, 10 pages.

* cited by examiner

APPARATUS FOR NONINVASIVE MEASUREMENT OF A HEART PERFORMANCE METRIC

CROSS-REFERENCE TO RELATED APPLICATIONS

This application claims the benefit of U.S. Application No. 62/723,242, filed on Aug. 27, 2018, the contents of which are incorporated herein by reference.

TECHNICAL FIELD

This disclosure relates generally to devices for measuring the performance of the heart, and in particular but not exclusively, relates to devices for measuring blood pressure, such as left ventricular filling pressure.

BACKGROUND INFORMATION

Heart failure (HF) is commonly defined as the inability of the heart to maintain an adequate circulation of blood, or the ability only to do so at the expense of increased filling pressures. HF is a grouping of clinical findings, rather than a specific diagnosis or a single disease, and can be considered a symptom of impairment of the pumping action and/or filling of the heart that is caused by an underlying disease. The circulation of blood is quantified by cardiac output, which is dependent on heart rate, contractility, preload, and afterload. Increased preload, driven by increased filling pressure, is one physiological response to increase cardiac output to meet the body's requirements. However, the elevated pressure leads to pulmonary congestion. Additional congestion occurs as fluid "backs up" in the venous system. As the congestion worsens, the resulting symptoms (dyspnea, orthopnea) become debilitating for the patient.

One conventional HF measurement device has been developed for the chronic monitoring of filling pressures, specifically the pulmonary arterial diastolic pressure as an estimate of the left-sided filling pressure. This device has demonstrated that filling pressures typically increase well before other heart failure symptoms become apparent, and studies have demonstrated that filling pressures can be used to effectively guide intervention and optimize therapy to improve outcomes. Unfortunately, this conventional HF measurement device is an invasive, implantable hemodynamic monitor that is restricted for use with only a subset of HF patients. The ability to perform filling pressure measurements non-invasively would broaden the selection criteria to potentially include the chronic monitoring and management of stable individuals with HF.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1A:
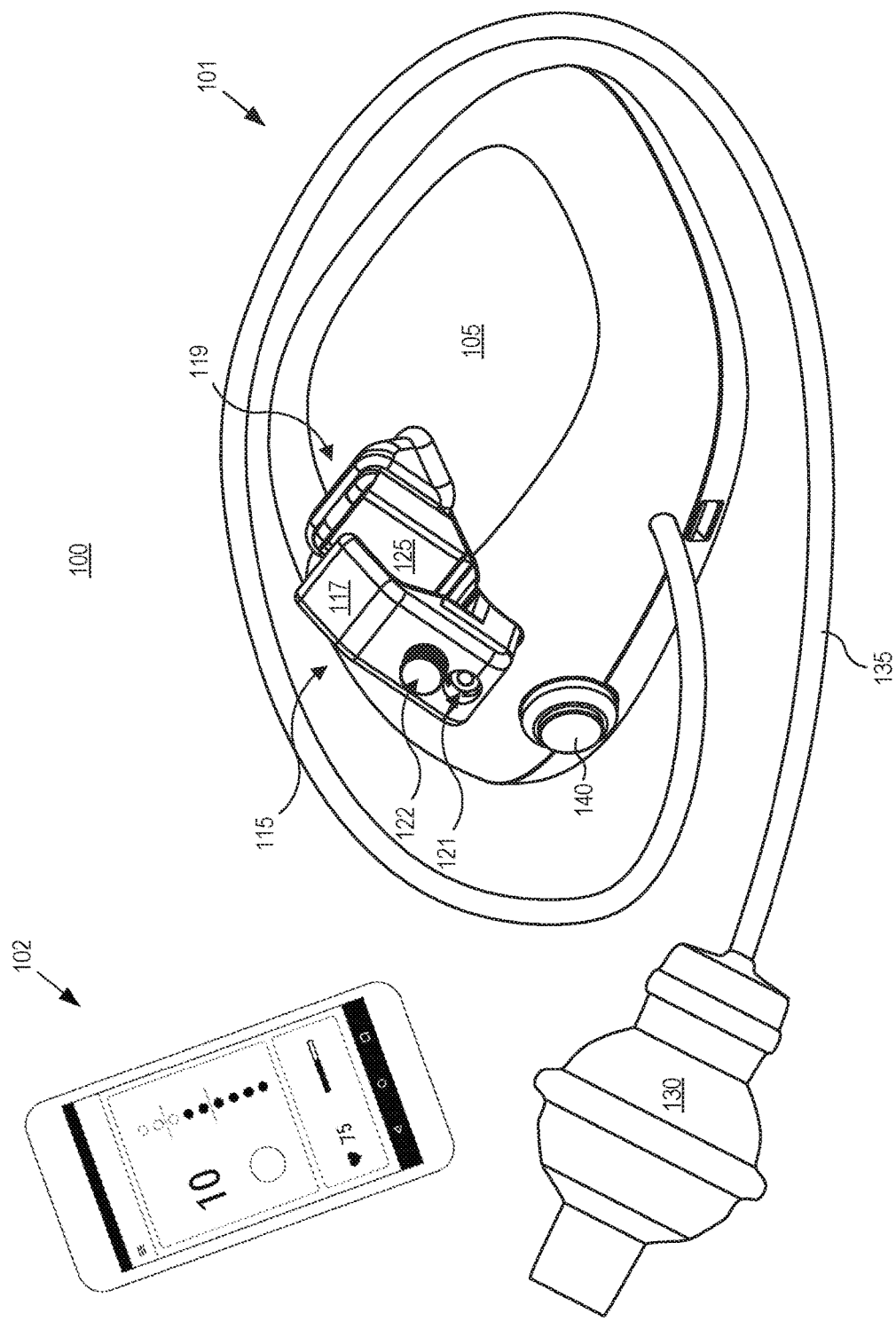
FIG. 1A illustrates a heart performance measurement system, in accordance with an embodiment of the disclosure.

Embodiments of a system, apparatus, and method for noninvasively measuring a heart performance metric, such as left ventricular filling pressure, are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

A heart performance measurement system capable of non-invasively measuring a performance metric of the heart, such as left ventricular filling pressure (e.g., left ventricular end diastolic pressure (LVEDP)), is described. These non-invasive measurements can be performed in an outpatient clinical setting or even at home. The described system provides a less invasive and less expensive alternative to conventional devices, which means it can be deployed more widely and make a significant impact in reducing both the financial cost and quality of life burden of heart failure (HF) in the general public. The heart performance measurement system is capable of monitoring filling pressure over time, which can be used to guide patient intervention and improve outcomes (e.g., defined as decreased rate of re-hospitalizations and improved quality of life metrics). The heart performance measurement system may be used for HF screening and diagnosis using filling pressure levels, pre-discharge therapeutic optimization of filling pressure levels, and chronic long-term monitoring at home. The heart performance measurement system provides a reproducible and predictable measurement of the arterial response to allow estimates of the absolute baseline filling pressure value as well as trending changes in the filling pressure over time. In various embodiments, the heart performance measurement system uses applanation tonometry of a digital artery to monitor the pulsatility of the arterial response. Due to the ease of use, high-compliance daily at home use is believed to be achievable.

In various embodiments, the heart performance measurement system measures filling pressure based on arterial blood pressure responses to increased intrathoracic pressure using a forced expiratory effort maneuver (e.g., Valsalva maneuver). The Valsalva maneuver raises intrathoracic pressure, diminishes venous return to the heart and stroke volume, and increases venous pressure. Arterial-pressure tracings (blood pressure pulsatility) generally show four distinct phases in response to the Valsalva maneuver performed by healthy individuals. In phase 1, the arterial pressure rises as a direct result of the transmission to the periphery of the increased intrathoracic pressure; in phase 2, reductions in systolic, diastolic, and pulse pressures occur as a result of reduced venous return with continuing strain; phase 3 begins with the release of the strain (e.g., cessation of expiratory effort), which results in a sudden drop in arterial pressure; and in phase 4 the arterial pressure overshoots to levels above control, with a widened pulse pressure. Additionally, at expiratory pressures >20 mmHg, the heart rate generally (but not always) increases during phase 2 and then decreases in phase 4. This expected pattern can be measured and analyzed in the user's blood pressure pulsatility signals acquired before, during, and after a forced expiratory effort maneuver.

Figure 1B:
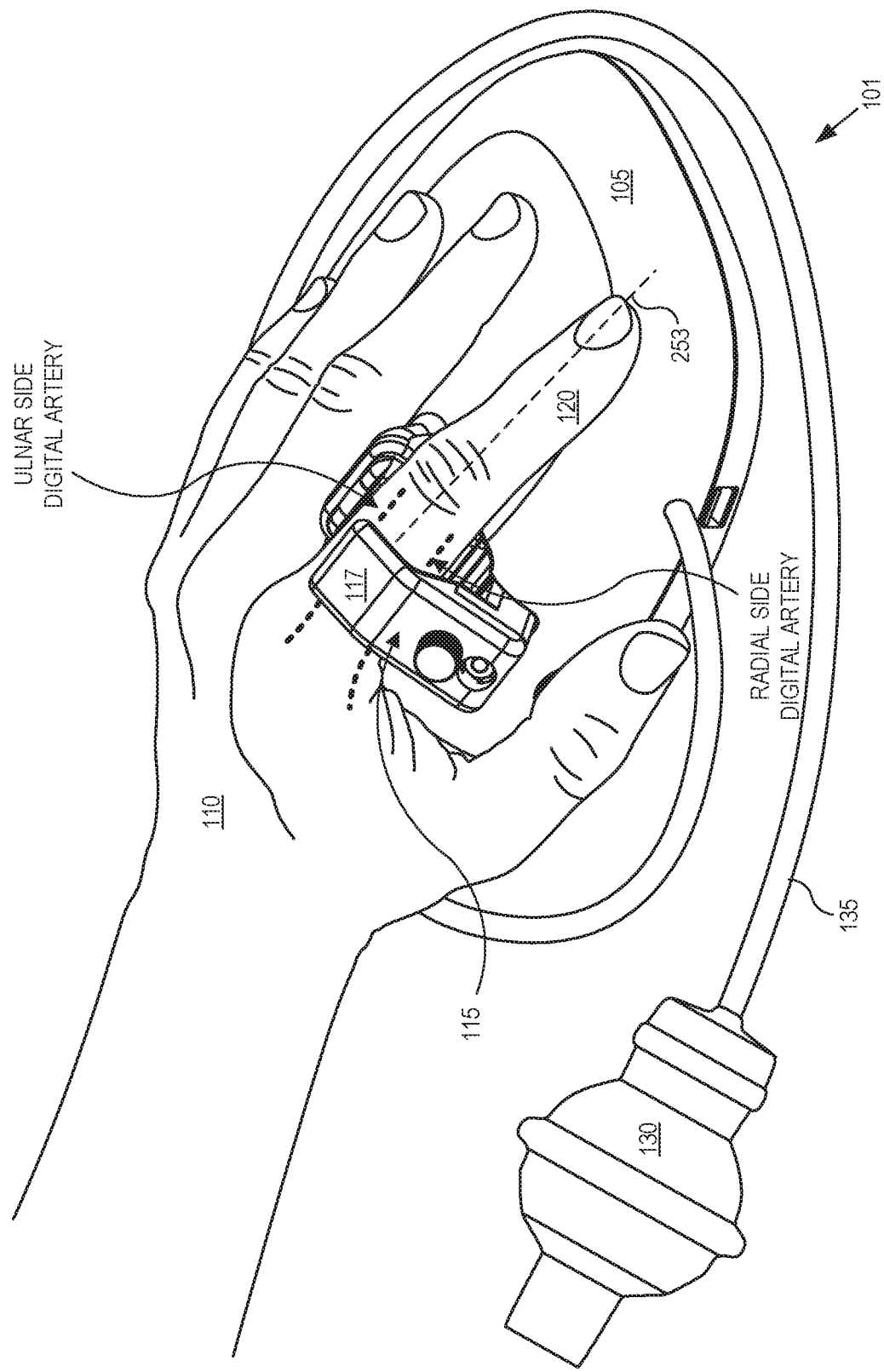
FIG. 1B illustrates a hand grasping a base unit of the heart performance measurement system, in accordance with an embodiment of the disclosure.

FIG. 1A illustrates a heart performance measurement system 100, in accordance with an embodiment of the disclosure. The illustrated embodiment of system 100 includes a base unit 101 and a software platform, which optionally may be executed in part on a mobile device 102 and/or on base unit 101. As illustrated in FIG. 1B, base unit 101 includes a housing 105 having a shape and a size that is conducive for grasping by a hand 110 during operation. The illustrated embodiment of base unit 101 includes a finger clamp 115 extending from housing 105 for applying a clamping force to finger 120. Finger clamp 115 applies the clamping force along a linear path to press a digital artery in finger 120 into a tactile sensor 125. The clamping force flattens the digital artery against tactile sensor 125, which measures blood pressure pulsatility in the digital artery via applanation tonometry. Base unit 101 further includes an expiratory subsystem (mouthpiece 130, air tube 135, and internal pressure sensor) into which the user blows (expires) during a heart performance test.

Figure 2A:
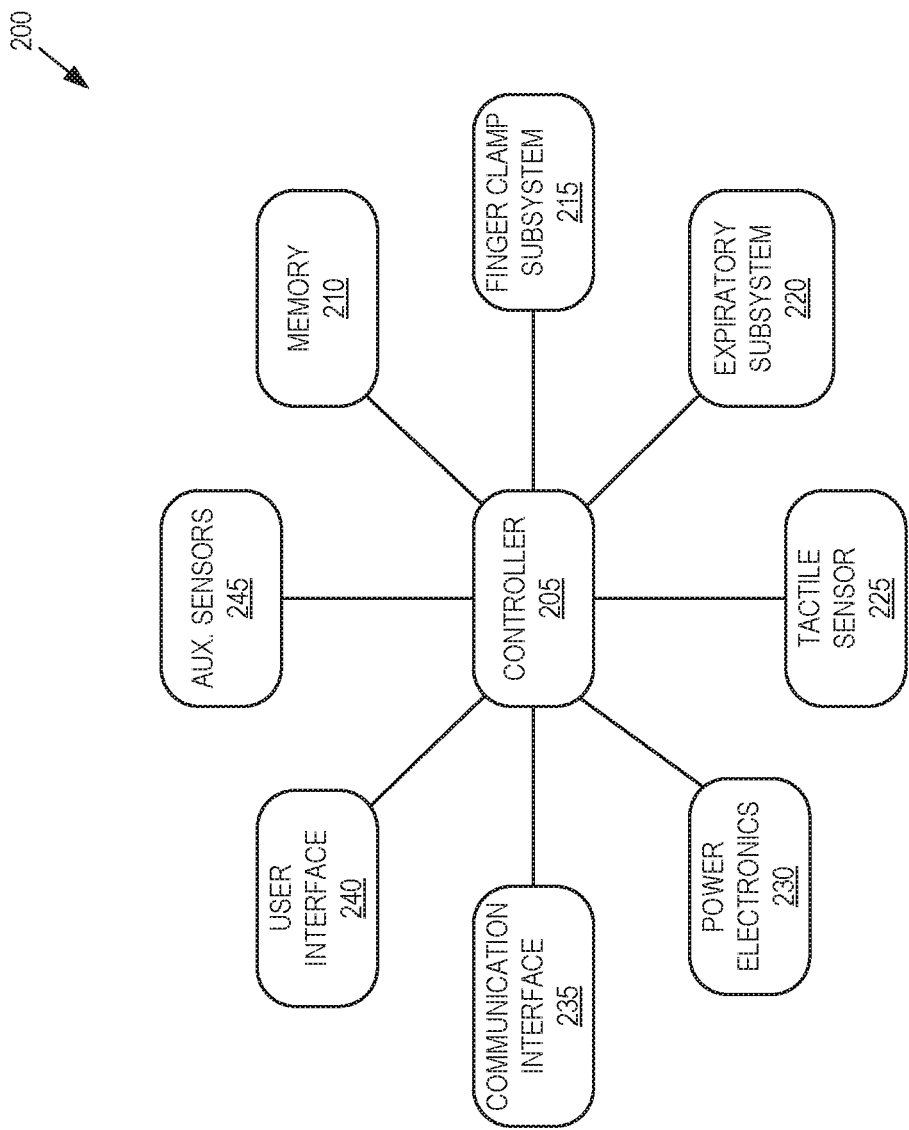
FIG. 2A is a functional block diagram illustrating various functional components of the heart performance measurement system, in accordance with an embodiment of the disclosure.

FIG. 2A is a functional block diagram illustrating functional components 200 of system 100, in accordance with an embodiment of the disclosure. The illustrated embodiment of components 200 includes a controller 205, memory 210, a finger clamp subsystem 215, an expiratory subsystem 220, a tactile sensor 225, power electronics 230, a communication interface 235, a user interface 240, and auxiliary sensors 245. System 100 illustrated in FIGS. 1A and 1B represents one possible physical implementation of components 200.

Controller 205 is a functional element that choreographs and controls the operation of the other functional elements. In one embodiment, controller 205 is implemented with hardware logic (e.g., application specific integrated circuit, field programmable gate array, etc.). In yet another embodiment, controller 205 may be implemented as a general purpose microcontroller that executes software or firmware instructions stored in memory 210 (e.g., non-volatile memory, etc.). Yet alternatively, controller 205 may be implemented in a combination of hardware and software and further may be centralized or distributed across multiple components.

Finger clamp subsystem 215 includes finger clamp 115, which in turn includes an adjustable jaw 117 and a fixed jaw 119 disposed opposite the adjustable jaw 117. Fixed jaw 119 protrudes from housing 105 and, in the illustrated embodiment, has a flat surface along which tactile sensor 125 is disposed. Tactile sensor 125 is disposed along the flat surface which rises from housing 105 at an oblique angle from the outer surface of housing 105 to accurately flatten the portion of finger 120 where the digital artery resides. In one embodiment, the angle of the flat surface is 50 degrees from horizontal. In other embodiments, the flat surface along which tactile sensor 125 is disposed may not be flat, but rather include curvature. In the illustrated embodiment, finger clamp 115 is oriented on housing 105 to measure blood pressure pulsatility from the ulnar side digital artery of an index finger 120. However, it should be appreciated that finger clamp 115 may be repositioned and reoriented on housing 105 to measure blood pressure pulsatility in the radial side digital artery of index finger 120, or to measure blood pressure pulsatility from other fingers or the thumb of hand 110. It should be appreciated that base unit 101 and specifically finger clamp 115 illustrated in FIGS. 1A and 1B represent merely one possible implementation of the functional components 200. Rather, base unit 101, and specifically finger clamp 115, may assume a variety of other shapes and configurations.

During operation, finger clamp 115 generates a clamping force directed along a linear path. Referring to FIG. 1A, adjustable jaw 117 fits into a track opening in housing 105 to permit adjustable jaw 117 to move in and out to apply the appropriate clamping force on finger 120 that flattens the digital artery for applanation tonometry. In one embodiment, the clamping force applied to finger 120 is sufficient to flatten the digital artery but does not fully occlude the digital artery (e.g., ulnar side digital artery) or the opposing digital artery (e.g., radial side digital artery). Rather, the linear actuation of finger clamp 115 is controlled to achieve static applanation (flattening), but not full occlusion or sweeping full occlusion to partial occlusion as is the case with traditional blood pressure meters with bladders or cuffs. In the illustrated embodiment, adjustable jaw 117 has a curved shape along its inside surface opposite tactile sensor 125 that cradles the side of finger 120 opposite tactile sensor 125. The curvature of adjustable jaw 117 serves to diffuse the clamping force over a broader surface area of finger 120 so as to reduce the likelihood of occlusion of the opposite side digital artery, or even the veins in finger 120, when finger 120 is clamped to flatten the near side digital artery (e.g., ulnar side digital artery in FIG. 1B). Not occluding the veins within finger 120 ensures there is a return path in finger 120 to maintain blood flow during the testing. Embodiments of finger clamp subsystem 215 and tactile sensor 225 are not limited to applanation tonometry. Other implementations of finger clamp subsystem 215 and/or tactile sensor 225 may use other techniques for sensing blood pressure pulsatility (e.g., PPG sensor, oscillometry, auscultation, etc.).

Figure 2B:
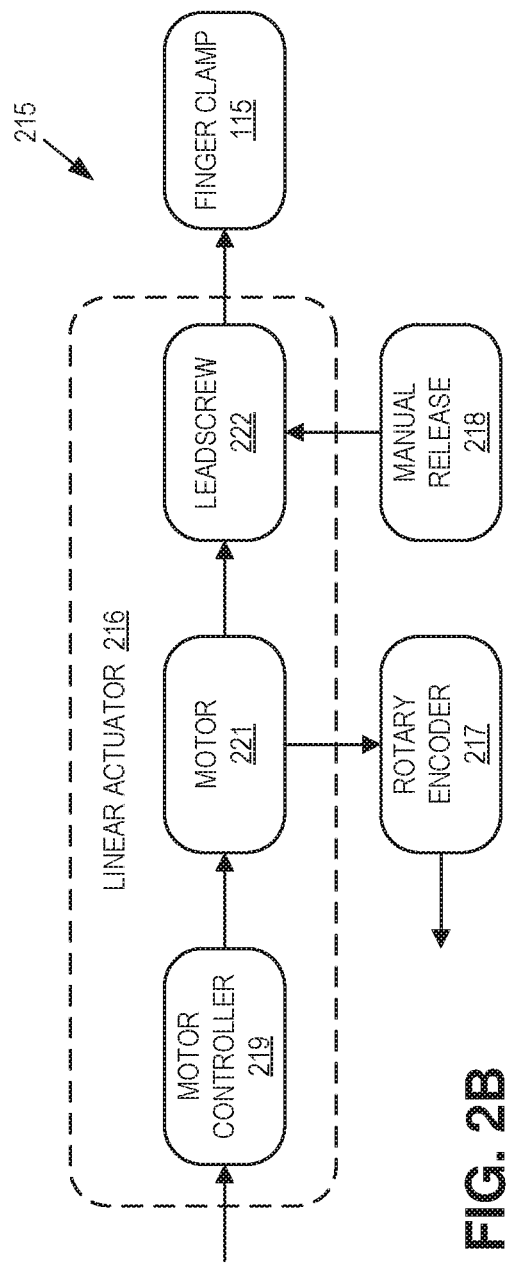
FIG. 2B is a functional block diagram illustrating various functional components of a finger clamp subsystem, in accordance with an embodiment of the disclosure.

FIG. 2B illustrates further details of finger clamp subsystem 215, in accordance with an embodiment of the disclosure. In the illustrated embodiment, finger clamp subsystem 215 includes a linear actuator 216, finger clamp 115, a rotary encoder 217, and a manual release 218. The illustrated embodiment of linear actuator 216 includes a motor controller 219, a motor 221, and a leadscrew 222. Linear actuator 216 is operated under the influence of controller 205 to apply the clamping force directed along a linear path. The rotary motion of motor 221 is translated into a linear motion via leadscrew 222. Referring to FIG. 1A, leadscrew 222 may mate with a mirror image worm gear 121 formed into adjustable jaw 115. Rotary encoder 217 is coupled to motor 221 to encode the absolute rotational position of motor 221 and leadscrew 220 and provide feedback control to controller 205 and/or motor controller 219. In other embodiments, an encoder-less design may be implemented that omits rotary encoder 217. For example, rotary encoder 217 may be omitted in favor of using a stepper motor or having motor controller 219 monitor the current draw of motor 221 to estimate motor velocity. The illustrated embodiment of finger clamp subsystem 215 further includes a manual release 218 that engages leadscrew 222 and provides a user with a manual release option. Referring to FIG. 1A, manual release 218 may be implemented as a manual release knob 122 that can be turned, pressed, or pulled to manually release adjustable jaw 117. In the illustrated embodiment, manual release knob 122 provides a manual gear drive for turning the leadscrew. Although the illustrated embodiments of finger clamp subsystem 215 are implemented with a linear actuator that applies a clamping force along a linear path, other types of actuators including non-linear actuators that apply a clamping force along linear or non-linear paths may also be implemented.

Figure 2D:
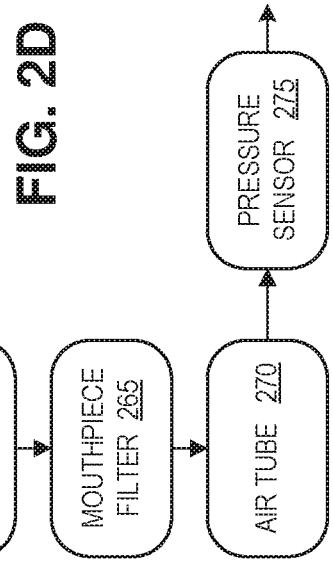
FIG. 2D is a functional block diagram illustrating various functional components of an expiratory subsystem, in accordance with an embodiment of the disclosure.
Figure 2C:
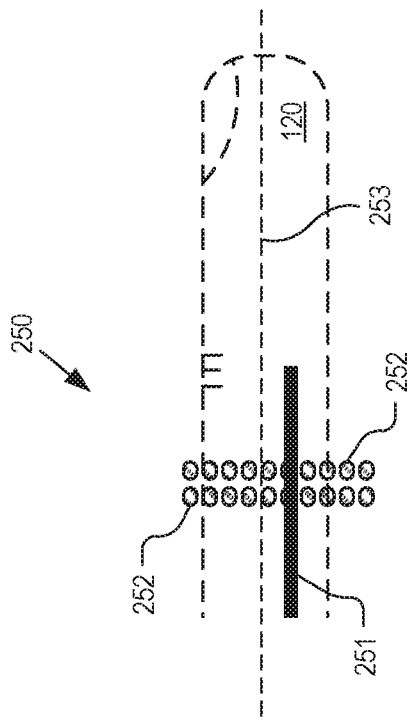
FIG. 2C illustrates a tactile sensor array for measuring blood pressure pulsatility, in accordance with an embodiment of the disclosure.

As mentioned above, tactile sensor 225 (or 125) is disposed along the flat surface of fixed jaw 119 to measure blood pressure pulsatility signals from a digital artery. FIG. 2C illustrates a tactile sensor array 250 for measuring blood pressure pulsatility in digital artery 251, in accordance with an embodiment of the disclosure. Tactile sensor array 250 is one possible implementation of tactile sensor 225 (or 125). Tactile sensor array 250 includes a plurality of individual sensor elements 252 organized into a two-dimensional (2D) array having more rows than columns, where the rows align substantially parallel to a longitudinal (axial) axis 253 of finger 120. The increased number of rows facilitates easier alignment across different users having fingers 120 of different sizes. In the illustrated embodiment, tactile sensor array 250 includes ten rows and two columns of sensor elements 252, though other numbers of rows and columns may be implemented. The individual sensor elements 252 may be implemented with various types of pressure sensors. In one embodiment, sensor elements 252 are capacitive sensor elements and tactile sensor array 250 is a capacitive sensor array. It is noteworth that FIG. 2C is not drawn to scale. In some embodiments, the sensor pitch between rows of sensor elements 252 may be selected so that multiple rows of sensor elements 252 overlap digital artery 251 at a given time and digital artery 251 cannot be lost between adjacent rows of sensor elements 252.

Heart performance measurement system 100 is capable of non-invasively measuring a performance metric of the heart, such as ventricular filling pressure, with a specific example being LVEDP. Returning to FIG. 2A, to measure filling pressure increased intrathoracic pressure using a forced expiratory effort maneuver (e.g., Valsalva maneuver) is used. Expiratory subsystem 220 facilitates the forced expiratory effort maneuver. FIG. 2D illustrates further details of expiratory subsystem 220, in accordance with an embodiment of the disclosure. In the illustrated embodiment, expiratory subsystem 220 includes a mouthpiece 260, a mouthpiece filter 265, an air tube 270, and a pressure sensor 275. Mouthpiece 260 may be shaped to permit a user to place their lips around and blow against resistance (e.g., see mouthpiece 130 in FIG. 1A). Mouthpiece filter 265 may be disposed at the base of mouthpiece 260 and acts as a spit filter to impede the migration of saliva into air tube 270 and housing 105. In a clinical setting, mouthpiece 260 and mouthpiece filter 265 may be disposable with mouthpiece filter 265 acting as a bacterial and viral filter. Air tube 270 couples the expiratory pressure to pressure sensor 275, which is disposed within housing 105. Pressure sensor 275 measures the expiratory effort in the form of air pressure and outputs pressure readings to controller 205. Mouthpiece 130 and air tube 135 illustrated in FIG. 1A represent one possible implementation of mouthpiece 260 and air tube 270, respectively. In another embodiment, pressure sensor 275 may be disposed within mouthpiece 260 and air tube 270 replaced with an electrical wire connection to base unit 101. In yet another embodiment, pressure sensor 275 may be integrated into mouthpiece 260 and a wireless connection to base unit 101 provided via communication interface 235. In the illustrated embodiment, pressure sensor 275 is integrated into base unit 101 and separate from mouthpiece 260.

The operator of system 100 interacts with the device via user interface 240. User interface 240 may include a variety of hardware and software interfaces. For example, user interface 240 may include one or more hardware buttons (e.g., button 140 in FIG. 1A) to enable the user to start or stop heart performance tests. Button 140 is positioned to align with the user's thumb when the index finger 120 is clamped in finger clamp 115. Alternatively (or additionally), button 140 may be integrated into mouthpiece 130 to be triggered by the other hand. Additionally, user interface 240 may include a graphical user interface (GUI) displayed on a screen. In FIG. 1A, the GUI is displayed on mobile device 102, which communicates with base unit 101 via a wireless or wired connection. In other embodiments (not illustrated), base unit 101 may include a display screen disposed on housing 105 along with associated hardware or software buttons to facility user interactions.

Base unit 101 may further include power electronics 230 to power the other electronic components. Power electronics 230 may include batteries and/or a power regulator for wired power. Communication interface 235 is provided within base unit 101 to provide external connectivity to mobile device 102 and/or cloud services. Communication interfaced 235 may include one or more of a Bluetooth adapter, a WiFi adapter, a USB adapter (illustrated in FIG. 1A), or otherwise.

Finally, base unit 101 may include other auxiliary sensors 245. For example, auxiliary sensors 245 may include an accelerometer disposed in base unit 101 to reject test readings when base unit 101 is being moved. Auxiliary sensors 245 may also include a temperature sensor disposed on housing 105 to measure the user's palm or finger temperature and store this data with the blood pressure pulsatility readings. In one embodiment, housing 105 may include a finger or palm heater to warm hand 110 and/or finger 120 to a desired temperature. Auxiliary sensors 245 may also include a photoplethysmography (PPG) sensor or a microphone disposed adjacent to finger clamp 115. The PPG and microphone may be supplemental sources for measuring pulsatility in finger 120. Other sensor types (e.g., optical sensors, ballistocardiography sensors, etc.) may also be incorporated.

Figure 3B:
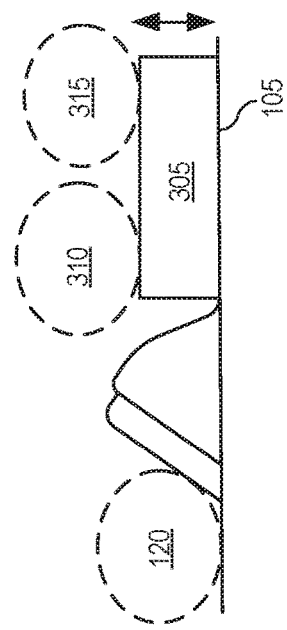
FIG. 3B is a side view illustration of a portion of the base unit illustrating how the alignment shim adjusts palm position, in accordance with an embodiment of the disclosure.
Figure 3A:
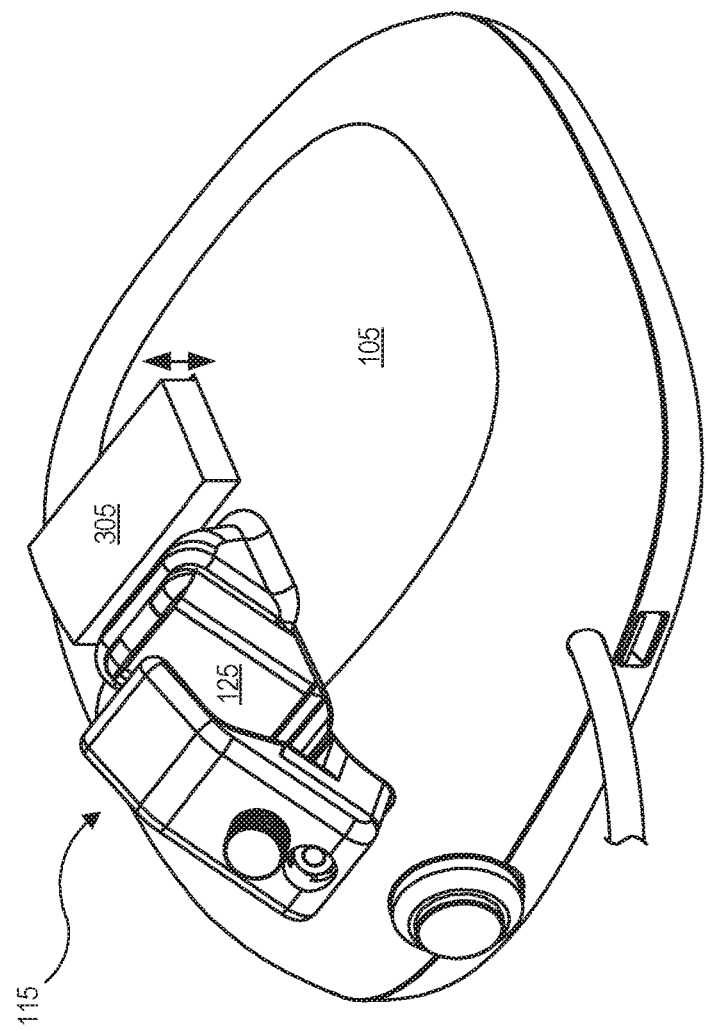
FIG. 3A is a perspective view illustration of the base unit including an alignment shim, in accordance with an embodiment of the disclosure.

FIGS. 3A-E illustrates various alignment features that may be integrated onto housing 105 to facility precise positioning of finger 120 within finger clamp 115. FIG. 3A illustrates an alignment shim 305 extending from housing 105, in accordance with an embodiment of the disclosure. Alignment shim 305 may be replaceable or adjustable to provide variable lift to fingers 310 and 315 (see FIG. 3B), which in turn adjusts a rotational position of the palm relative to finger clamp 115 while hand 110 is grasping housing 105. Rotating the palm in turn rotates index finger 120 about longitudinal axis 253 to fine tune alignment to tactile sensor 125.

Figure 3C:
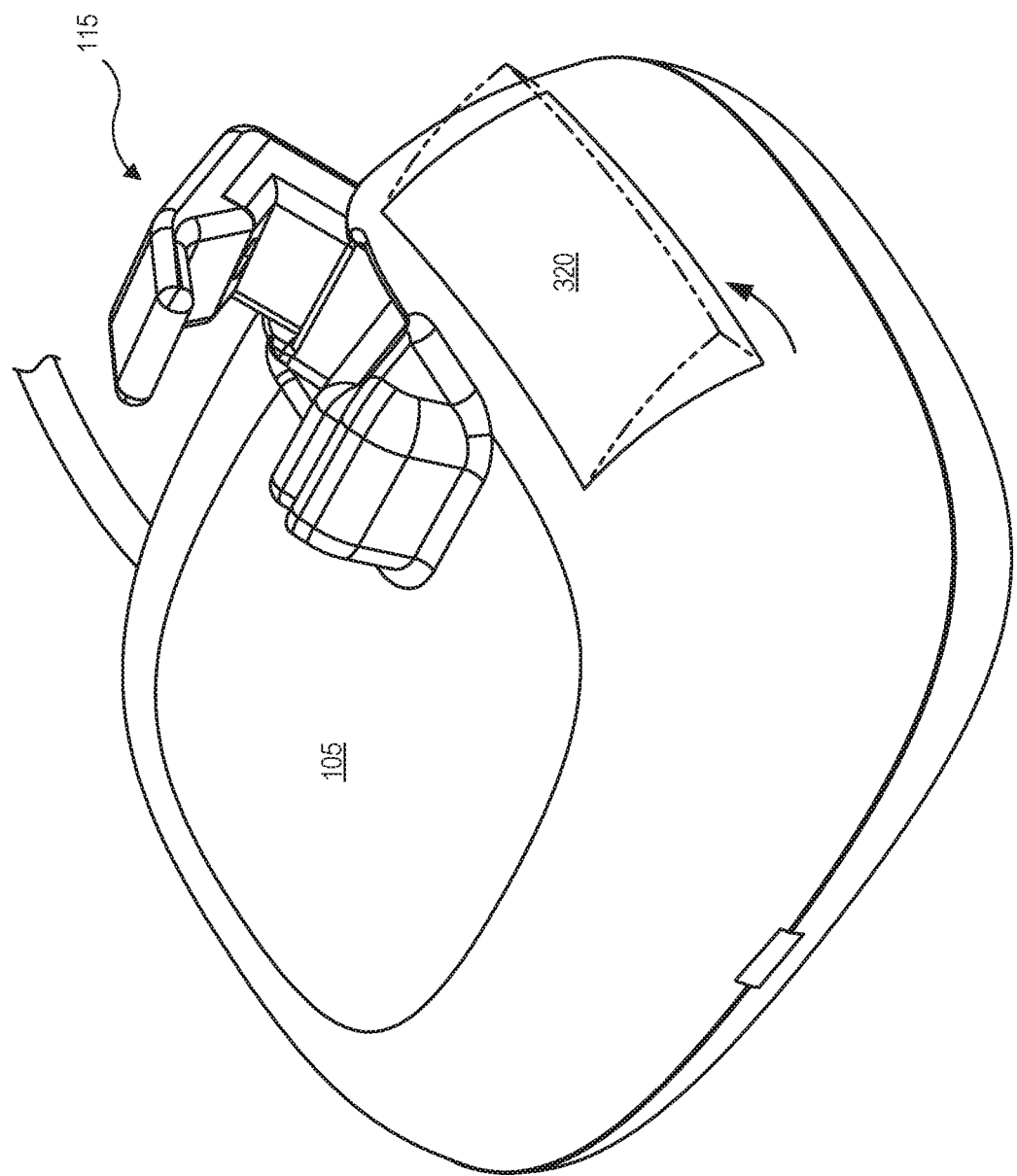
FIG. 3C is a perspective view illustration of the base unit including another alignment shim, in accordance with an embodiment of the disclosure.

FIG. 3C illustrates another alignment shim 320 extending from housing 105, in accordance with an embodiment of the disclosure. Alignment shim 320 may be replaceable or adjustable to provide variable lift directly to the palm, which in turn adjusts a rotational position of finger 120 in finger clamp 115 while hand 110 is grasping housing 105. The rotational adjustment provided by alignment shim 320 may be substantially orthogonal to the rotational adjustment provided by alignment shim 305. These adjustments may help tailor the exterior contour shape of housing 105 to different hand sizes and shapes to achieve improved alignment of the digital artery with tactile sensor 125.

Figure 3D:
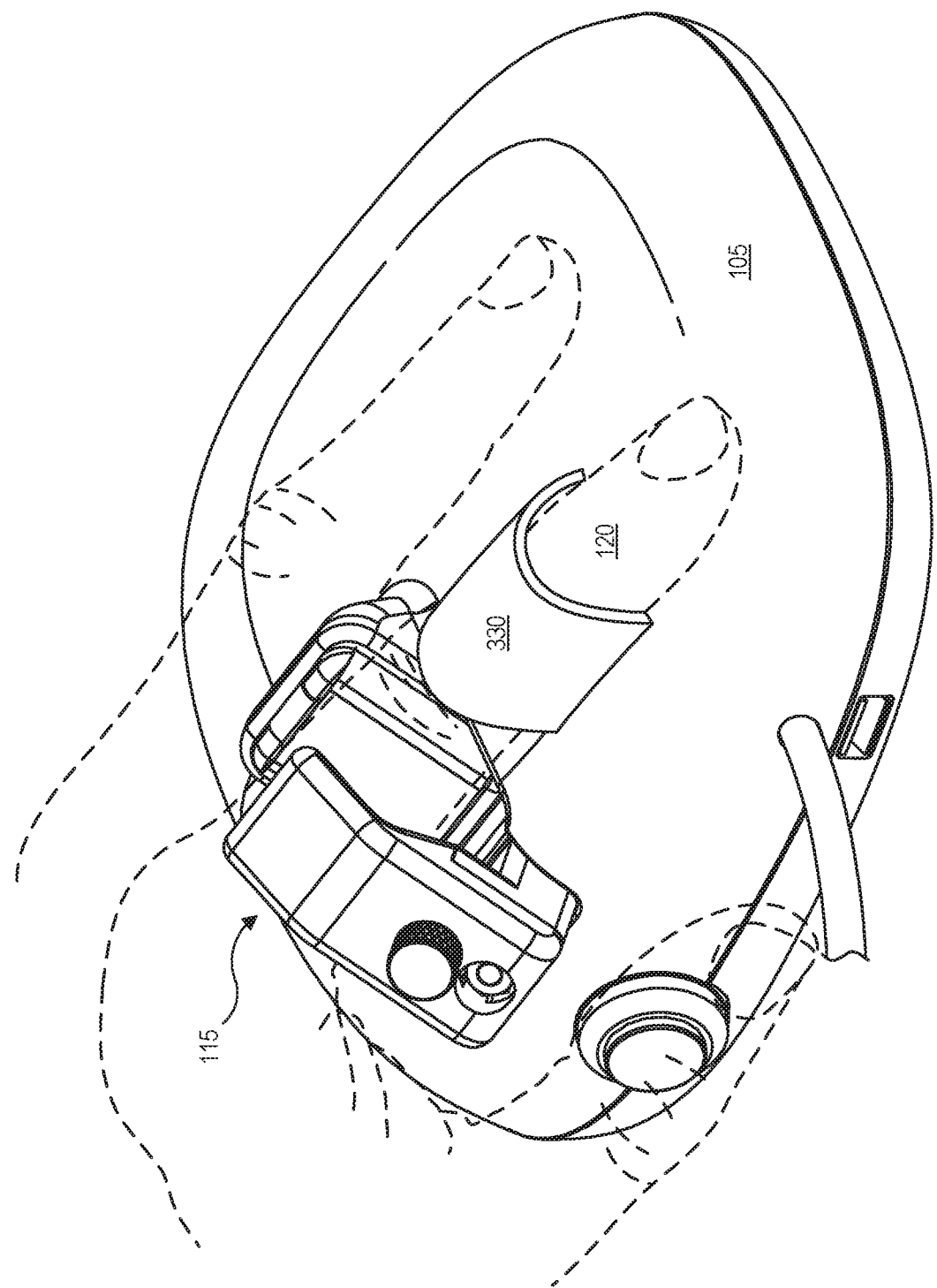
FIG. 3D is a perspective view illustration of the base unit including a finger holster for locating and securing a portion of the finger that extends past the finger clamp, in accordance with an embodiment of the disclosure.

FIG. 3D illustrates a finger holster 330 for locating and securing a portion of finger 120 that extends past finger clamp 115, in accordance with an embodiment of the disclosure. In one embodiment, finger holster 330 is formed of an elastic material and sized to provide a snug fit to finger 120. In one embodiment, a PPG sensor may be integrated into or under finger holster 330.

Figure 3E:
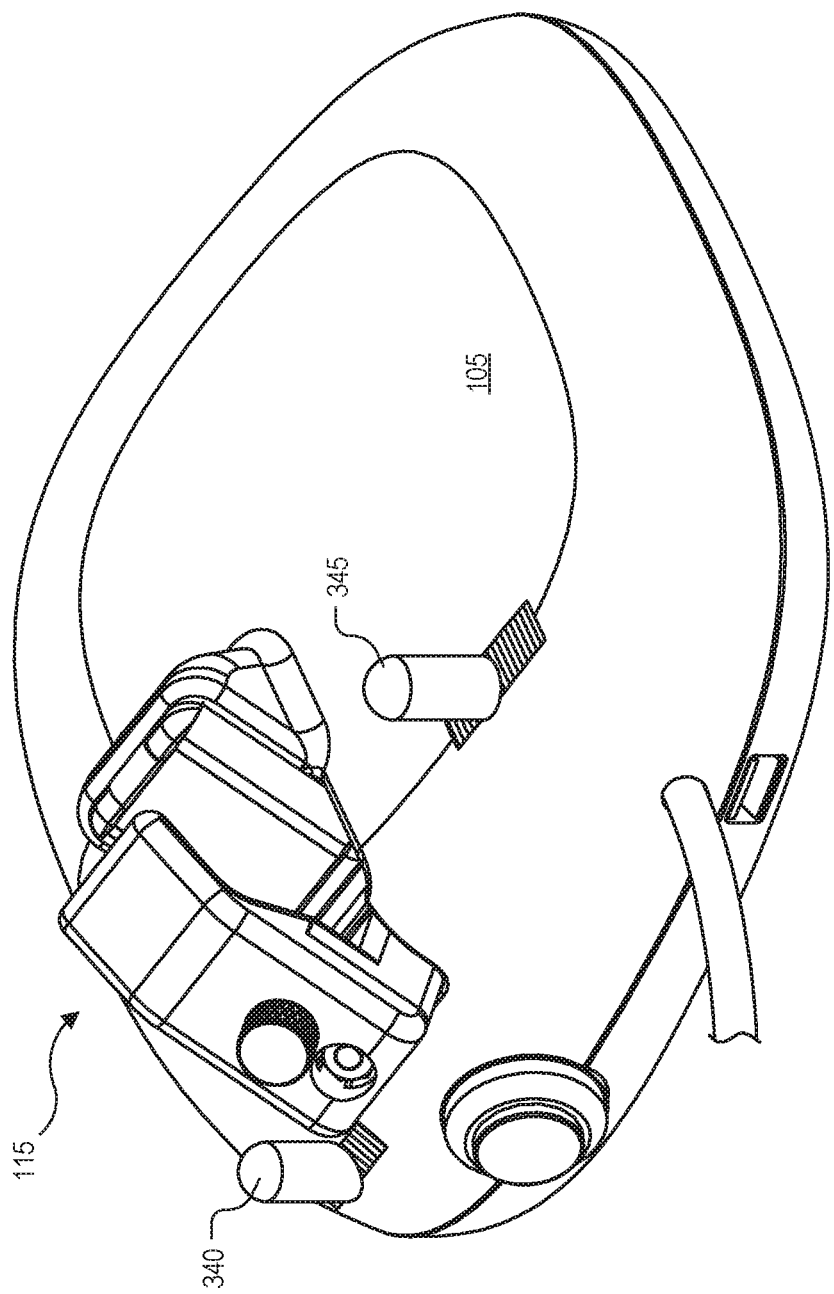
FIG. 3E is a perspective view illustration of the base unit including a finger web stop and a fingertip stop to aid finger alignment and positioning in the finger clamp, in accordance with an embodiment of the disclosure.

FIG. 3E illustrates a finger web stop 340 and a fingertip stop 345 to aid finger alignment and positioning in finger clamp 115, in accordance with an embodiment of the disclosure. Finger web stop 340 extends from housing 105 and is positioned to be cradled by a finger web while finger 120 is positioned in finger clamp 115. In the illustrated embodiment, the finger web is the web between the thumb and index finger; however, finger web stop 340 may also be positioned to align with other finger webs. Fingertip stop 345 also extends from housing 105 and is positioned to abut against a tip of finger 120 when finger 120 is positioned in finger clamp 115. Finger web stop 340 and/or fingertip stop 345 serve to locate the axial position of finger 120 within finger clamp 115 and may be used together or individually in isolation. In various embodiments, both finger web stop 340 and fingertip stop 345 may be mounted on sliders that include detents for selectable adjustment. Other adjustability mechanisms may be implemented.

All or some of the alignment features illustrated in FIGS. 4A-E may be incorporated in various combinations within a single implementation of system 100. These alignment features may be user adjustable at home or calibrated in a practitioner's office as part of a one-time user fitting.

Housing 105 of base unit 101 has an overall size and shape that is conducive to grasping by hand 110. In the illustrated embodiment, housing 105 has a computer mouse-like shape that can be rested on a tabletop while being grasped by hand 110 with an arm also resting on the tabletop during measurements. This configuration serves to encourage the user to relax and not move their hand during testing. In other embodiments, housing 105 may be shaped for being grasped and held adjacent to the user's chest. Other form factors may also be implemented.

Figure 4A:
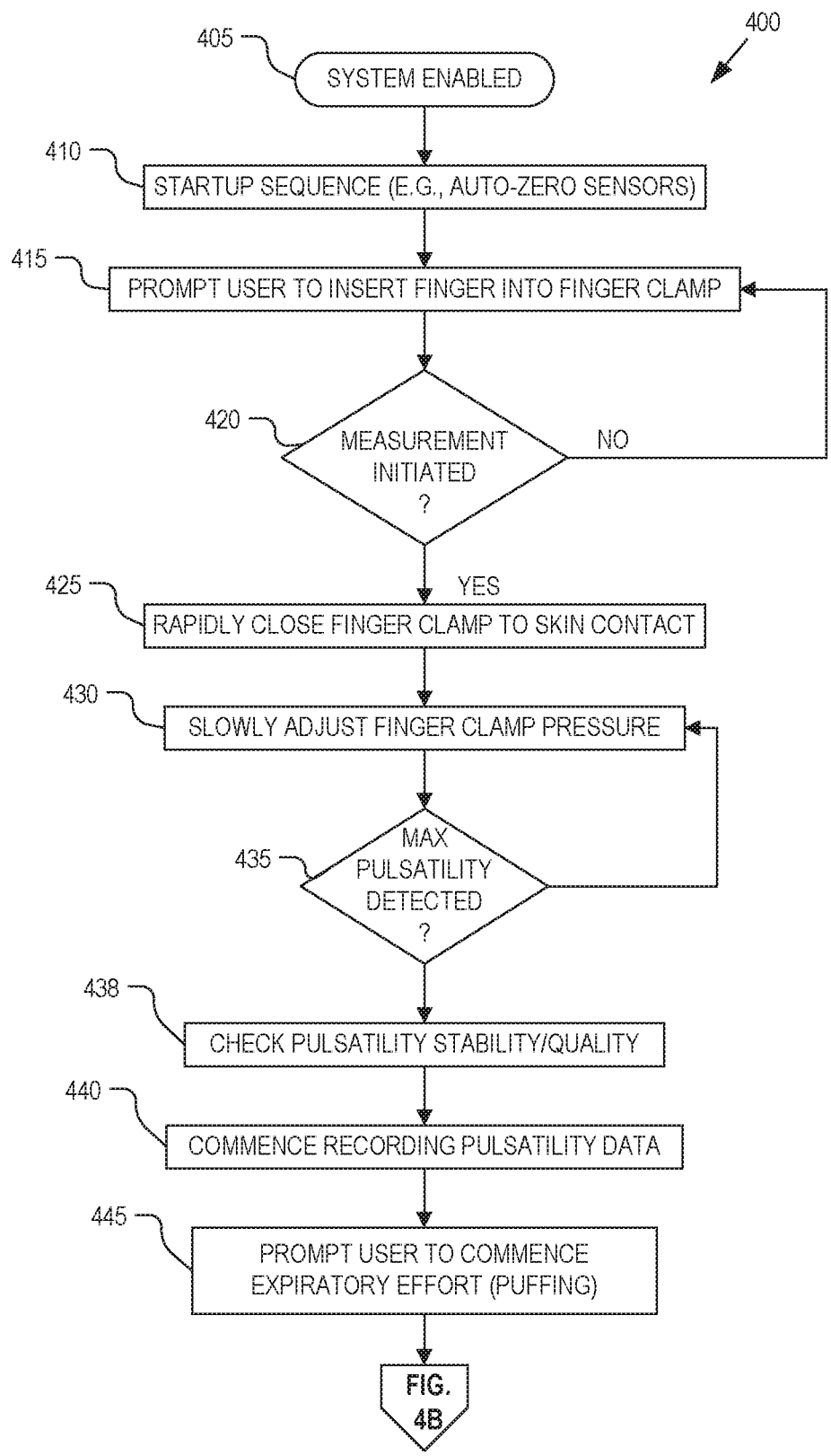
FIGS. 4A and 4B are a flow chart illustrating operation of the heart performance measurement system, in accordance with an embodiment of the disclosure.
Figure 4B:
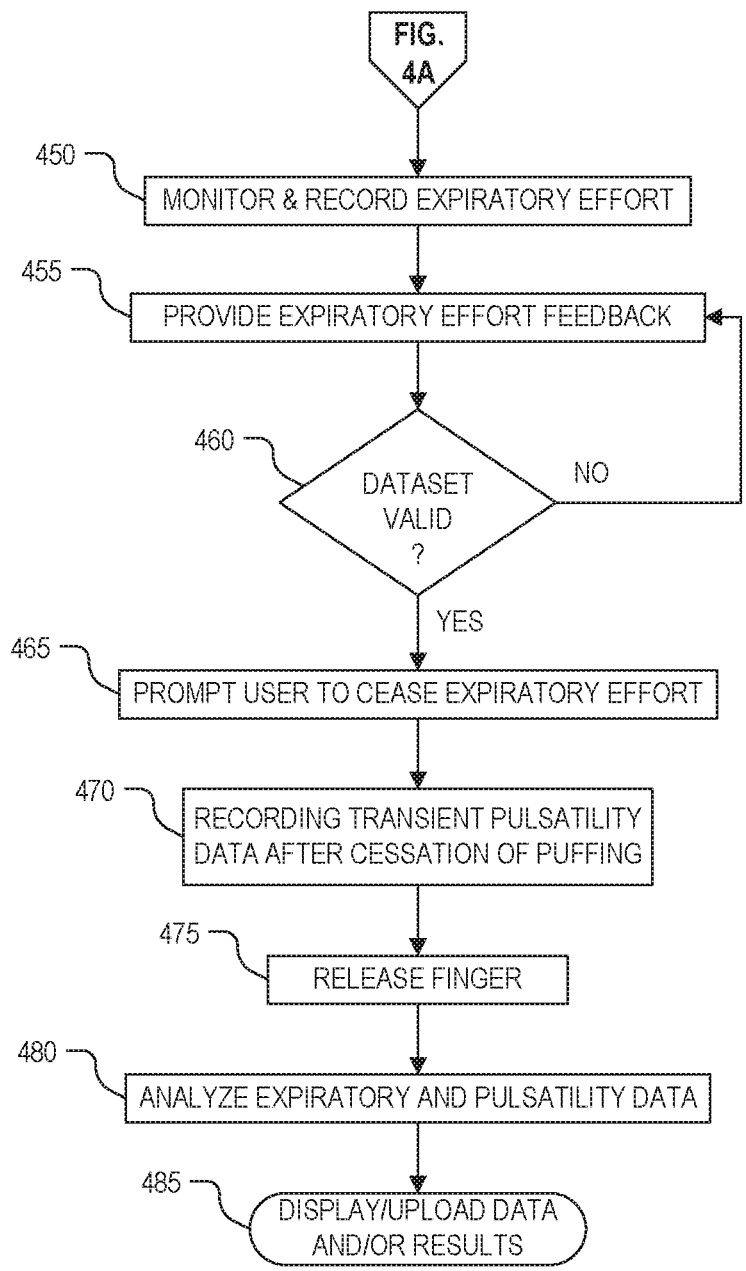

FIGS. 4A and 4B are a flow chart 400 illustrating operation of heart performance measurement system 100, in accordance with an embodiment of the disclosure. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

In a process block 405, system 100 is enabled. Enabling system 100 may be achieved with an initial press of thumb button 140, or by pressing a software button on the GUI interface displayed on mobile device 102. Enabling system 100 causes system 100 to execute a self-test or startup sequence that auto-zeros various sensors including sensor elements 252 in tactile sensor array 250, linear actuator 216, pressure sensor 275, etc. (process block 410). The self-test is performed before the user places finger 120 into finger clamp 115.

In a process block 415, the user is prompted by user interface 240 to insert their finger into finger clamp 115. The prompt may be a message displayed on mobile device 102, a message displayed on a screen integrated into housing 105, an audible prompt, or otherwise. Once the user has inserted their finger into finger clamp 115 and grasped housing 105, a measurement may be user initiated (decision block 420) via another press of thumb button 140 or a soft button displayed on mobile device 102. The user's grips need not be firm, but rather in some embodiments, may be a light grip sufficient for the hand to generally conform to the shape of housing 105.

Upon initiation of a heart performance test, controller 205 directs linear actuator 216 to rapidly close finger clamp 115 until light skin contact between finger 120 and tactile sensor 125 is registered (process block 425). Once light skin contact is registered, controller 205 reduces the adjustment speed of linear actuator 216 to a slower speed setting (process block 430) during which the appropriate clamping force is determined for applanation tonometery. The appropriate clamping force is the force that flattens the digital artery proximal to tactile sensor 125. This appropriate or optimal clamping force is determined by slowly increasing the clamping force while monitoring the amplitude of the blood pressure pulsatility signals sensed from the digital artery. As the clamping force is increased, the blood pressure pulsatility signals should increase up to a maxim, then begin to decrease. Once the amplitude begins to decrease, controller 205 determines that maximum pulsatility has been detected (decision block 435) and backs off linear actuator 216 to the position associated with the detected maximum pulsatility. Once linear actuator 216 has been positioned for maximum pulsatility, it maintains a constant clamping force during the filling pressure testing. Rotary encoder 217 may be used during the pressure sweep to register the position associated with maximum pulsatility. The ramping range may be optimized or refined on a per user basis to reduce measurement time. Additionally, a stability check and/or pulsatility quality check may be performed at the determined set point for maximum pulsatility by observing pulses for a finite period of time, such as 2-10 seconds (process block 438).

With the finger clamp 115 adjusted to the set point associated with the determined maximum pulsatility and pulsatility stability/quality determined, controller 205 commences recording blood pressure pulsatility data (process block 440) from tactile sensor 125 into memory 210. In other embodiments, the pulsatility data is also recorded during the stability check to obtain a baseline reference of the blood pressure pulsatility prior to commencing the expiratory maneuver. After recording has commenced, the user is prompted to commence expiratory effort (process block 445). Expiratory effort includes the user puffing or blowing into mouthpiece 130, 260. The user's expiratory effort is monitored and recorded by controller 205 using pressure sensor 275 (process block 450). The effort level, rise time, duration, and stability may all be monitored/recorded. In a process block 455, the user is provided with real-time feedback for guiding their expiratory effort into a threshold effort range and holding it there for a threshold period of time (e.g., 10 seconds) needed for the heart performance test (e.g., LVEDP test). In one embodiment, an expiratory effort meter is displayed to the user via user interface 240. The user interface 240 may be displayed on mobile device 102 via wireless communication to base unit 101 or output on a display panel integrated into housing 105.

Figure 5A:
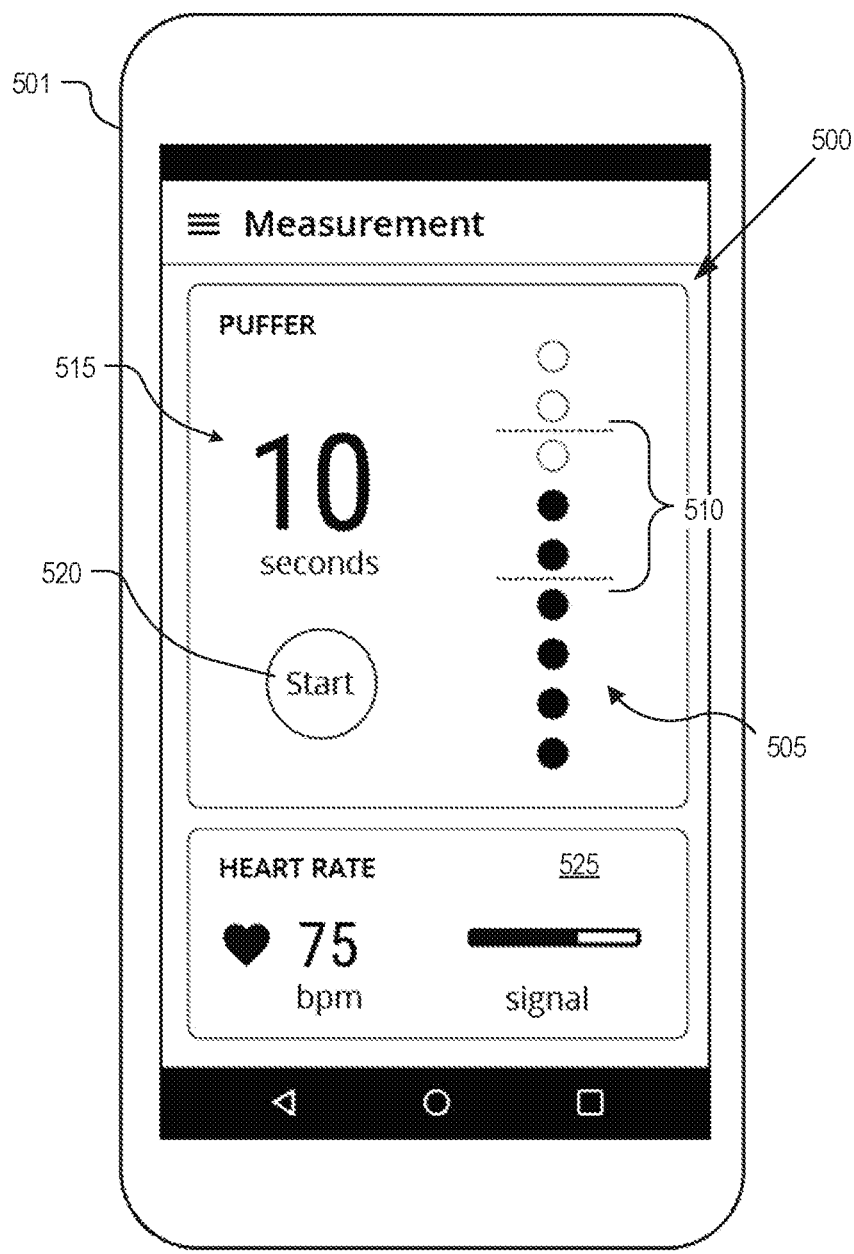
FIG. 5A illustrates an example graphical user interface for orchestrating operation of the heart performance measurement system, in accordance with an embodiment of the disclosure.
Figure 5B:
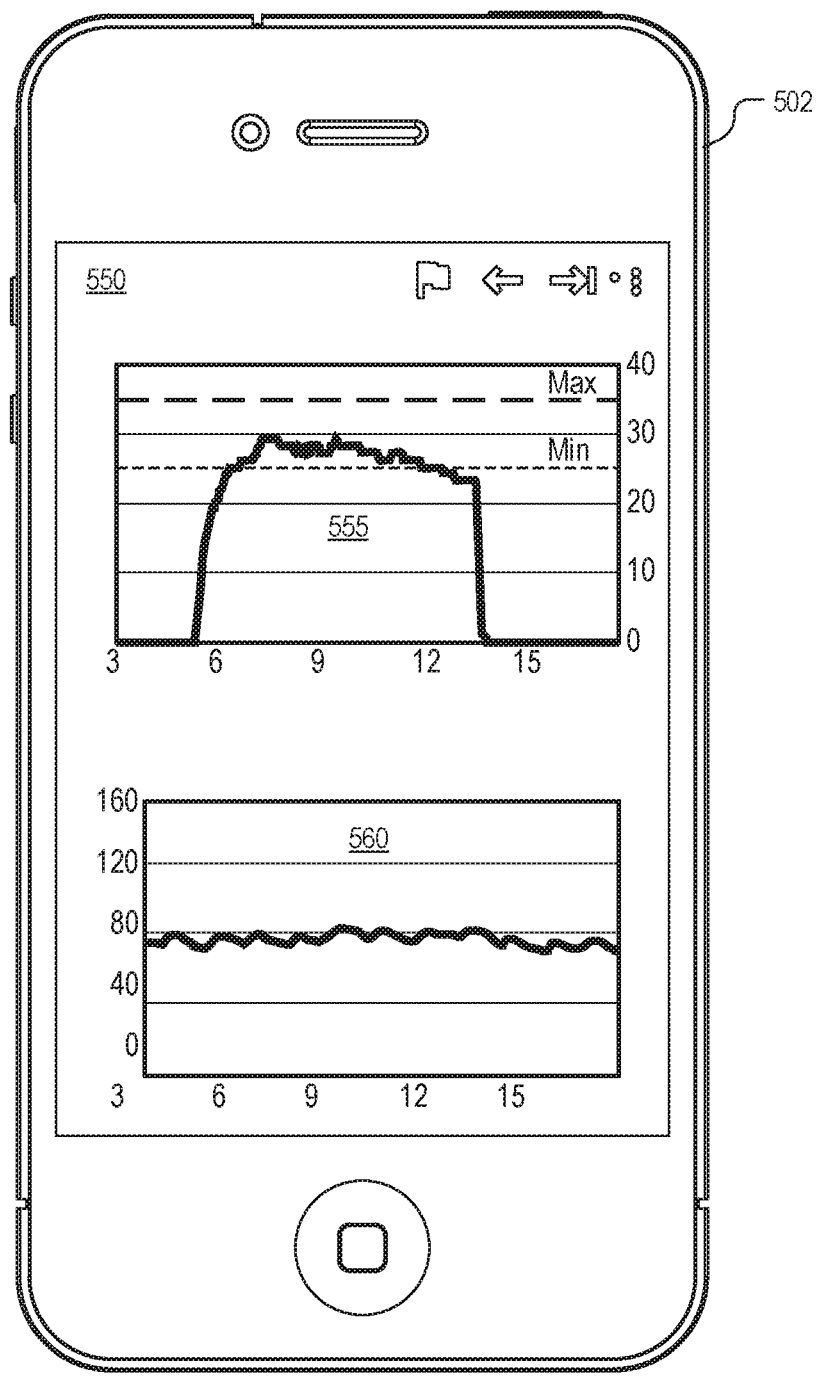
FIG. 5B illustrates another example graphical user interface for orchestrating operation of the heart performance measurement system, in accordance with an embodiment of the disclosure.

FIG. 5A illustrates an example user interface 500 displayed on a mobile device 501. As illustrated, user interface 500 includes an expiratory effort meter 505 including a threshold effort range 510. The user's expiratory effort is measured based upon air pressure. User interface 500 also includes a puffing timer 515 that counts down while the user's expiratory effort remains in threshold effort range 510. A soft start/stop button 520 is also provided to commence or terminate a heart performance test. User interface 500 also includes a pulsatility meter 525 that displays a real-time indication of the quality of the blood pulsatility signals received from tactile sensor 125, and in the illustrated embodiment also displays heart rate. Pulsatility meter 525 provides the user with a visual confirmation that their finger 120 is correctly positioned in finger clamp 115. FIG. 5B illustrates an example user interface 550 displayed on a mobile device 502, which may be considered a diagnostic display option. User interface 550 includes an expiratory effort meter 555 and pulsatility meter 560 both displayed as real-time active charts.

Returning to process 400 illustrated in FIG. 4B, once the requisite amount of data has been captured with the user's expiratory effort residing in the threshold effort range 510 (decision block 460), the user is prompted to cease expiratory effort (process block 465). Controller 205 continues to record the blood pressure pulsatility data even after the user ceases expiratory effort (process block 470). For example, controller 205 may continue to record data for 20 seconds post puffing as the transient pulsatility data is a relevant data for determining the filling pressure. Once the post puffing transient pulsatility data has been recorded, finger 120 is released (process block 475) and the expiratory and pulsatility data analyzed by controller 205 (process block 480). The data may be analyzed for deviations from expected signal waveforms for a healthy heart, similarities to characteristic traits, changes or deviations over time from a baseline measurement or pattern, etc. Particular shape characteristics may further be analyzed (e.g., dichrotic notch, frequency content, etc.). In one embodiment, machine learning (ML) may be applied to analyze the waveforms and estimate the filling pressure or other cardiac features. Furthermore, when analyzing the pulsatility data, data recorded from auxiliary sensors 245 may also be analyzed to supplement, augment, replace, or validate the pulsatility data. Finally, in a process block 485, the pulsatility data, expiratory data, and/or analysis results may be displayed to the user, saved locally for future reference, or uploaded to a cloud-based service. In one embodiment where the user is a patient under the supervision of a doctor or practitioner, the results may be automatically reported to the doctor/practitioner. Although process 400 illustrates a technique for measuring a filling pressure such as LVEDP, other heart performance metrics may also be measured/monitored with system 100. Such metrics may include REM sleep activity, systolic and diastolic blood pressure, overnight respiratory activity, variations in cardiac output with respiratory cycles, etc.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus for measuring a performance metric of a heart, the apparatus comprising:
   a housing;
   a tactile sensor adapted to measure blood pressure pulsatility in a digital artery of a finger via applanation tonometry and output pulsatility signals indicative of the blood pressure pulsatility, wherein the tactile sensor is disposed on a flat surface that protrudes from the housing at an oblique angle from an outer surface of the housing;

a finger clamp including an adjustable jaw extending from an opening in the housing and configured to move along a linear path to clamp the finger against the tactile sensor with the digital artery aligned over the tactile sensor;

a linear actuator configured to drive the adjustable jaw along the linear path to apply a clamping force; and a controller coupled to the tactile sensor and the linear actuator and adapted to control the clamping force and to generate pulsatility data, based upon the pulsatility signals, from which the performance metric of the heart may be determined.

2. The apparatus of claim 1, wherein the housing has a size and a shape which allows for the housing to be grasped by a hand.

3. The apparatus of claim 2, wherein the finger clamp is positioned and oriented on the housing to clamp an index finger while the housing is grasped by the hand and the tactile sensor is positioned and oriented to measure the blood pressure pulsatility from an ulnar side digital artery of the index finger.

4. The apparatus of claim 3, further comprising:
a user interface disposed on a side of the housing and positioned to be reachable by a thumb of the hand while the index finger is clamped in the finger clamp, the user interface coupled to the controller to enable a user to start or stop a measurement of the performance metric of the heart.

5. The apparatus of claim 2, further comprising one or more of:
one or more alignment shims extending from the housing and configured to adjust a rotational position of a palm of the hand relative to the finger clamp while the hand is grasping the housing;
a finger web stop extending from the housing and positioned to be cradled by a finger web of the finger is positioned in the finger clamp, wherein the finger web stop is adjustable to alter an axial position of the finger relative to the finger clamp;
a fingertip stop extending from the housing and positioned to abut against a tip of the finger when the finger is positioned in the finger clamp, wherein the fingertip stop is adjustable to alter the axial position of the finger relative to the finger clamp; or
a finger holster extending from the housing and positioned on the housing to locate and secure a portion of the finger that extends past the finger clamp.

6. The apparatus of claim 2, wherein the housing is shaped to rest on a tabletop while enabling the hand to grasp the housing while an arm connected to the hand is also resting on the tabletop during measurement of the performance metric of the heart.

7. The apparatus of claim 1, wherein the finger clamp has a curved shape configured to cradle a side of the finger located opposite the tactile sensor when the finger is positioned in the finger clamp.

8. The apparatus of claim 7, wherein the controller includes logic that when executed by the controller causes the apparatus to perform operations including:
clamping the finger to a sufficient enough pressure to measure the blood pressure pulsatility in the digital artery via applanation tonometry while not fully occluding the digital artery or an opposing digital artery of the finger.

9. The apparatus of claim 1, wherein the linear actuator comprises:

a motor disposed with the housing to generate a rotational force;
a leadscrew coupled to an output of the motor to translate the rotational force to the clamping force directed along the linear path, wherein the leadscrew extends into and engages with the adjustable jaw of the finger clamp.

10. The apparatus of claim 9, wherein the finger clamp further comprises:
a manual release knob extending from the adjustable jaw of the finger clamp, wherein the manual release knob engages with the leadscrew and provides a manual release of the clamping force when turned, pressed, or pulled.

11. The apparatus of claim 1, wherein the apparatus is adapted to measure a left ventricular end diastolic pressure (LVEDP) and wherein the apparatus further comprises:
a mouthpiece shaped to receive an expiration of a user;
an air tube connecting the mouthpiece to the housing; and
a pressure sensor disposed within the housing and coupled to the air tube to measure an air pressure of the expiration, wherein the controller is coupled to the pressure sensor and adapted to monitor the air pressure while generating the pulsatility data.

12. The apparatus of claim 1, wherein the tactile sensor comprises a two dimension capacitive sensor array having more rows than columns, wherein the rows align parallelly to a longitudinal axis of the finger when the finger is clamped in the finger clamp.

13. The apparatus of claim 1, further comprising:
a wireless communication interface disposed within the housing and coupled to the controller, wherein the controller is adapted to wirelessly communicate with a remote device to provide a graphical user interface for orchestrating a test of the performance metric of the heart and displaying results of the test, wherein the graphical user interface includes:
an expiratory effort meter for displaying when a user is exerting appropriate expiratory effort; and
a pulsatility meter for displaying when the blood pressure pulsatility is being sensed by the tactile sensor.

14. The apparatus of claim 1, wherein the tactile sensor is mounted to the housing and wherein the linear actuator and the controller are disposed at least partially within the housing.

15. At least one non-transitory machine-accessible storage medium that provides instructions that, when executed by a system, will cause the system to perform operations comprising:
linearly actuating an adjustable jaw of a finger clamp along a linear path to apply a clamping force to a finger to flatten a digital artery for applanation tonometry, wherein the adjustable jaw moves linearly in and out of an opening in a housing from which the finger clamp extends to clamp the finger externally to the housing while a hand including the finger grasps an exterior of the housing;
monitoring pulsatility signals output from a tactile sensor disposed in or on an inward-facing surface of the finger clamp; and
generating pulsatility data, based upon the pulsatility signals, from which a performance metric of the heart may be determined.

16. The at least one non-transitory machine-accessible storage medium of claim 15, further providing instructions that, when executed by the system, will cause the system to perform further operations, comprising:

monitoring an expiratory effort while monitoring the pulsatility signals;
recording the pulsatility data while the expiratory effort is within a threshold range; and
recording the pulsatility data following cessation of the expiratory effort.

17. The at least one non-transitory machine-accessible storage medium of claim 16, further providing instructions that, when executed by the system, will cause the system to perform further operations, comprising:
analyzing the pulsatility data recorded during the expiratory effort and recorded following the expiratory effort to determine the performance metric, wherein the performance metric comprises a left ventricular end diastolic pressure (LVEDP); and
displaying a result of the analyzing.

18. The at least one non-transitory machine-accessible storage medium of claim 16, further providing instructions that, when executed by the system, will cause the system to perform further operations, comprising:
prompting a user to commence the expiratory effort after sensing pulsatilty signals;
displaying an expiratory effort meter that provides real-time feedback for guiding the expiratory effort into the threshold effort range;
prompting the user to cease the expiration effort; and
linearly actuating the finger clamp to release the clamping force.

19. The at least one non-transitory machine-accessible storage medium of claim 16, further providing instructions that, when executed by the system, will cause the system to perform further operations, comprising:
displaying a pulsatility meter in real-time indicating whether the pulsatility signals from the tactile sensor are registering blood pressure pulsatility in the digital artery of the finger.

20. At least one non-transitory machine-accessible storage medium that provides instructions that, when executed by a system, will cause the system to perform operations comprising:
linearly actuating a finger clamp to apply a clamping force along a linear path to a finger to flatten a digital artery for applanation tonometry;
monitoring pulsatility signals output from a tactile sensor disposed in or on an inward-facing surface of the finger clamp; and
generating pulsatility data, based upon the pulsatility signals, from which a performance metric of the heart may be determined,
wherein the linearly actuating the finger clamp to apply the clamping force along the linear path to flatten the digital artery for applanation tonometry comprises:
closing the finger clamp along the linear path at a first speed until the tactile sensor registers skin contact; and
adjusting the clamping force applied by the finger clamp along the linear path at a second speed, slower than the first speed, after the tactile sensor registers the skin contact.

21. The at least one non-transitory machine-accessible storage medium of claim 20, wherein the adjusting the clamping force at the second speed comprises:
adjusting the clamping force to identify a clamping force setting that provides a maximal pulsatility amplitude.

22. An apparatus for measuring a performance metric of a heart, the apparatus comprising:
a housing;
a tactile sensor adapted to measure blood pressure pulsatility in a digital artery of a finger via applanation tonometry and output pulsatility signals indicative of the blood pressure pulsatility;
a finger clamp extending from the housing and configured to clamp the finger against the tactile sensor with the digital artery aligned over the tactile sensor;
a linear actuator configured to drive the finger clamp with a clamping force directed along a linear path; and
a controller coupled to the tactile sensor and the linear actuator and adapted to control the clamping force and to generate pulsatility data, based upon the pulsatility signals, from which the performance metric of the heart may be determined,
wherein the tactile sensor is disposed on a flat inward-facing surface of the finger clamp and the finger clamp includes a curved shape opposing the flat inward-facing surface, the curved shape configured to cradle a side of the finger and press the finger towards the flat inward-facing surface along the linear path,
wherein the flat inward-facing surface protrudes from the housing at an oblique angle from an outer surface of the housing.

\* \* \* \* \*